United States Patent [19]

Slater

[11] Patent Number: 5,417,709
[45] Date of Patent: May 23, 1995

[54] ENDOSCOPIC INSTRUMENT WITH END EFFECTORS FORMING SUCTION AND/OR IRRIGATION LUMENS

[75] Inventor: Charles R. Slater, Fort Lauderdale, Fla.

[73] Assignee: Symbiosis Corporation, Miami, Fla.

[21] Appl. No.: 226,701

[22] Filed: Apr. 12, 1994

[51] Int. Cl.⁶ .............................................. A61B 17/42
[52] U.S. Cl. .................. 606/205; 606/207; 604/27
[58] Field of Search ............... 606/205–211; 604/19, 27, 36, 93, 115–117

[56] References Cited

U.S. PATENT DOCUMENTS

| | | | |
|---|---|---|---|
| 2,397,823 | 4/1946 | Walter . | |
| 3,019,790 | 2/1962 | Militana | 606/205 |
| 3,980,086 | 9/1976 | Kletschka | 604/27 |
| 4,646,751 | 3/1987 | Maslanka . | |
| 4,750,488 | 6/1988 | Wuchinich et al. | 604/27 |
| 4,763,668 | 8/1988 | Macek et al. . | |
| 4,880,015 | 11/1989 | Nierman . | |
| 5,016,614 | 5/1991 | MacAllister | 604/93 |
| 5,123,902 | 6/1992 | Müller et al. | 604/27 |
| 5,131,379 | 7/1992 | Sewell, Jr. | 606/205 |
| 5,141,519 | 8/1992 | Smith et al. | 606/205 |
| 5,152,778 | 10/1992 | Bales, Jr. et al. | 606/205 |
| 5,195,958 | 3/1993 | Phillips | 604/33 |
| 5,197,968 | 3/1993 | Clement | 604/93 |
| 5,209,747 | 5/1993 | Knoepfler | 606/16 |
| 5,217,460 | 6/1993 | Knoepfler | 606/205 |
| 5,224,931 | 7/1993 | Kumar | 604/51 |
| 5,286,255 | 2/1994 | Weber | 604/22 |
| 5,300,087 | 4/1994 | Knoepfler | 606/207 |
| 5,312,391 | 5/1994 | Wilk | 606/205 |

Primary Examiner—C. Fred Rosenbaum
Assistant Examiner—Perry E. Van Over
Attorney, Agent, or Firm—David P. Gordon

[57] ABSTRACT

An endoscopic instrument with suction/irrigation end effectors includes a tube, a push rod which extends through the tube, an actuator engaging the tube and the push rod, and end effectors coupled to the tube and push rod, where the end effectors include or define a bore which acts as a lumen for suction/irrigation. A fluid conduit in the tube communicates with the bore in the end effectors and is coupled to a suction or irrigation source. In one embodiment, a pair of end effectors are each coupled to a separate irrigation/suction conduit which is fed through the tube. The proximal ends of the conduits are coupled to one or separate fluid couplings at the proximal end of the instrument for connection with suction/irrigation sources. In another embodiment, a stationary end effector is provided with a fluid bore which is coupled to a fluid conduit integral with the tube. In both of these embodiments, the fluid bore(s) terminate(s) in one or more openings on a surface of the end effector(s) so that suction/irrigation is provided on a surface of the end effector(s). In a third embodiment, the annulus between the push rod and the tube acts as a fluid conduit for suction/irrigation and each end effector is provided with a longitudinal surface groove which defines a lumen therebetween so that suction/irrigation may be performed when the end effectors are in the closed position.

18 Claims, 3 Drawing Sheets

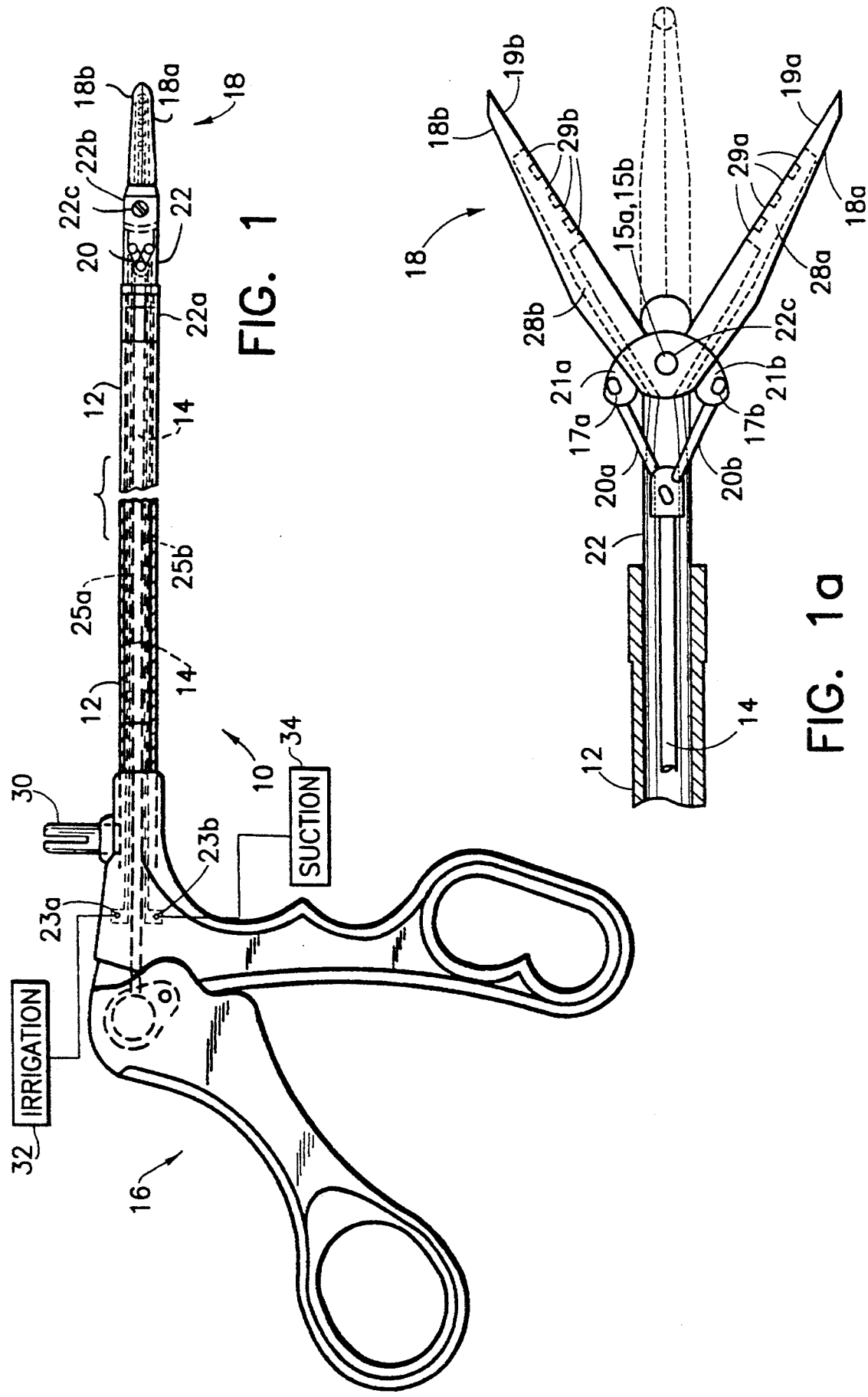

ENDOSCOPIC INSTRUMENT WITH END EFFECTORS FORMING SUCTION AND/OR IRRIGATION LUMENS

BACKGROUND OF THE INVENTION

1. Field of the Invention

The invention relates to endoscopic instruments. More particularly, the invention relates to endoscopic instruments having single or double acting end effectors wherein one or both of the end effectors are provided with or define one or more lumens for suction and/or irrigation.

2. State of the Art

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. A camera, magnifying lens, or other optical instrument is often inserted through a first trocar tube, while a cutter, dissector, or other surgical instrument is inserted through another trocar tube for purposes of manipulating and/or cutting the internal organ. Sometimes it is desirable to have several trocar tubes in place at once in order to receive several surgical instruments. In this manner, organs or tissue may be grasped with one surgical instrument, and simultaneously may be cut with another surgical instrument; all under view of the surgeon.

By 1996, it is expected that more than two million additional endosurgeries will be performed per year that, in 1990, were done via open surgery (MedPRO Month, I:12, p.178). The advantages of endoscopic surgery are clear in that it is less invasive, less traumatic and recovery is typically quicker. As a result, many new instruments and devices for use in endosurgery are introduced every year.

Endoscopic surgical instruments generally include a tube, a push rod which extends through the tube, an actuating means which engages the tube and the push rod and which imparts reciprocal axial motion to the push rod, and end effector means coupled to the distal end of the tube and to the distal end of the push rod by a clevis. Axial movement of the push rod effects movement of the end effector means in a plane parallel to the longitudinal axis of the push rod. For purposes herein, the "distal end" of a surgical instrument or any part thereof, is the end most distant from the surgeon and closest to the surgical site, while the "proximal end" of the instrument or any part thereof, is the end most proximate the surgeon and farthest from the surgical site.

There are many different types of end effectors used in various endoscopic surgical instruments, e.g. grippers, cutters, scissors, jaws, etc. Moreover, end effectors may be either single acting (a first end effector element remains stationary while a second end effector element is rotated relative to the first) or double acting (both end effector elements are rotated relative to each other).

As mentioned above, during endoscopic surgery, several trocar tubes may be used to allow the use of several different tools simultaneously. In addition to a camera and various surgical instruments, it is often desirable to provide suction and/or irrigation conduits during surgery. Such conduits, which can be flexible tubes, must also be delivered to the surgical site through a trocar tube. While it is generally appreciated that the number of trocar tubes used should be kept to a minimum, it is also the general rule that only one surgical instrument or tool can be inserted through a trocar tube at any given time. Moreover, when several trocar tubes are used, it becomes difficult for the surgeon to simultaneously locate several surgical instruments at the surgical site. For example, during a particular operation, it may be desirable to provide suction and/or irrigation at the surgical site while simultaneously cutting or gripping an organ or tissue. Such a procedure typically requires at least three trocar tubes (one for the camera, one for the cutting or gripping tool, and one for the suction/irrigation tool), and the surgeon must use both hands to guide the suction and/or irrigation conduit to the site where the cutting or gripping tool is in use.

SUMMARY OF THE INVENTION

It is therefore an object of the invention to provide an endoscopic surgical instrument which allows for the precise location of suction and/or irrigation functions at the surgical site.

It is also an object of the invention to provide an endoscopic instrument having multiple functions in order to reduce the number of trocar tubes needed for an endoscopic surgical procedure.

It is another object of the invention to provide an endoscopic instrument having workable end effectors which also provide suction and/or irrigation capabilities.

It is still another object of the invention to provide suction and/or irrigation capabilities in an endoscopic surgical instrument having either single acting or double acting end effectors.

In accord with these objects which will be discussed in detail below, the endoscopic instrument of the present invention broadly comprises a tube, an actuating means engaging the tube, and end effector means coupled to the actuating means and to the tube, wherein the end effector means define or are provided with one or more internal bores which act as lumens for suction and/or irrigation. The tube itself, or one or more fluid conduits located in the tube, communicates with the bore(s) defined by or provided in the end effector means to provide suction and/or irrigation, and an irrigation source, or vacuum source is coupled, typically by a valve, to the tube or fluid conduit.

In one embodiment of the invention having double acting end effectors, each end effector is provided with a bore. The bores are in turn coupled to the distal ends of separate irrigation/suction conduits which are fed through the tube of the instrument alongside the actuating means. The proximal ends of the conduits are coupled to one or separate fluid couplings at the proximal actuating means of the instrument for connection with suction and/or irrigation sources. In another embodiment of the invention having single acting end effectors, the stationary end effector is provided with a fluid bore which is coupled to a fluid conduit built into the tube of the instrument. The fluid conduit terminates at a proximal end of the instrument with a fluid coupling for connection with a suction or irrigation source. In both of these embodiments, the distal portion of the fluid bore(s) terminate(s) in one or more openings on a surface portion of the end effector(s) so that suction and/or irrigation is provided on a surface portion of the end effector(s). In a third embodiment of the invention, the annular space between the push rod and the tube of the instruments acts as a fluid conduit for suction and/or irrigation. In this embodiment, the end effectors are provided with one or more longitudinal surface grooves which extend to the distal ends of the end effectors so that the suction and/or irrigation may be performed when the end effectors are in the closed position.

According to preferred aspects of the invention, the actuating means of the invention which actuates the end effectors comprises a handle and a push rod which is coupled to the handle. At the distal end of the instrument, a clevis is provided. The clevis is coupled both to the distal end of the tube and to the proximal ends of the end effector means which rotate thereabout. The clevis thereby translates axial movement of the push rod to the rotational movement of the end effectors in a plane parallel to the longitudinal axis of the push rod.

Additional objects and advantages of the invention will become apparent to those skilled in the art upon reference to the detailed description taken in conjunction with the provided figures.

BRIEF DESCRIPTION OF THE DRAWINGS

FIG. 1 is a partially schematic, and partially broken side elevation view in partial section of a first embodiment of the invention;

FIG. 1a is an enlarged broken side elevation view in partial section of the end effectors of the embodiment of FIG. 1;

DETAILED DESCRIPTION OF THE PREFERRED EMBODIMENTS

Figure 1C:
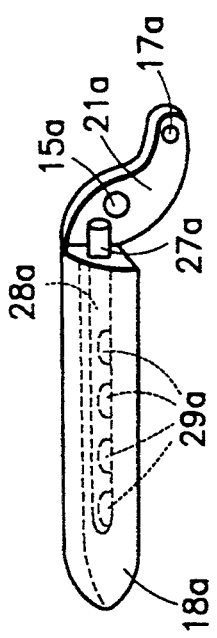
FIG. 1c is an enlarged perspective view of one of the end effectors of the embodiment of FIG. 1.
Figure 1B:
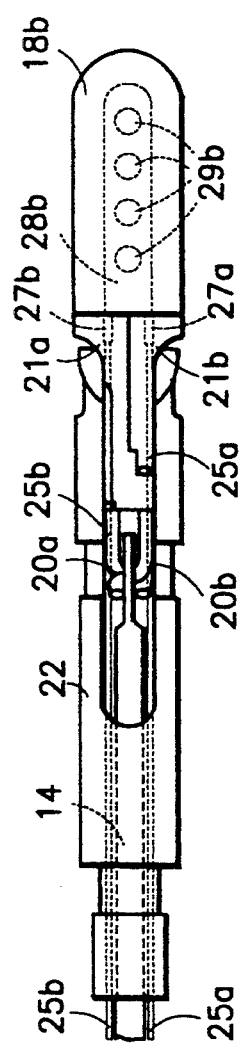
FIG. 1b is an enlarged broken top view of the end effectors of the embodiment of FIG. 1.

Referring now to FIGS. 1 and 1a–1c, the endoscopic instrument 10 of the present invention generally includes an outer tube 12, a push rod 14 which extends through the tube 12, an actuating means 16 engaging the tube 12 and the push rod 14 for imparting reciprocal axial motion to the push rod 14, end effector means 18 coupled to the push rod 14 by linkage means 20, and a clevis 22 coupled to the tube 12 at its proximal end 22a and to the end effector means 18 at its distal end 22b. As seen in the Figures, end effector means 18 comprises a pair of end effectors 18a, 18b, each of which is provided with a pivot hole 15a, 15b, a tang 21a, 21b, and a linkage coupling hole 17a, 17b. End effectors 18a, 18b are mounted for rotation on clevis pin 22c which passes through the pivot holes 15a, 15b. The linkage means 20 comprises a pair of articulating links 20a, 20b which couple the distal end of the push rod 14 with the tangs 21a, 21b of the end effectors 18a, 18b through coupling holes 17a, 17b. This arrangement provides that axial movement of the push rod 14 effects rotational movement of the end effector means 18 in a plane parallel to the longitudinal axis of the push rod 14. Such movement of the end effector means 18 is best seen in FIG. 1a where the end effector means is shown in the open position and the phantom lines indicate the closed position. The endoscopic instrument 10, as shown in FIG. 1, may also be provided with an electrical contact 30 which is electrically coupled to the hollow tube 12. By coupling a source of electrical current to contact 30, the end effectors 18a, 18b can be made "hot" for electrocautery procedures. Regardless of whether the tool 10 has electrocautery capabilities, the tube 12 is preferably covered with a shrink wrap tubing 13.

According to a first embodiment of the invention, the end effector means 18 include a double acting pair of end effectors 18a, 18b. Each end effector 18a, 18b is provided with an internal bore 28a, 28b acting as a lumen for suction and/or irrigation. Each bore 28a, 28b, terminates at one end with one or more fluid openings 29a, 29b located on an inner face surface 19a, 19b of the end effector The other end of each bore 28a, 28b, preferably terminates in a first fluid coupling 27a, 27b in a proximal end of the end effector 18a, 18b alongside the end effector tang 21a, 21b. Each fluid coupling 27a, 27b is coupled to a flexible fluid conduit 25a, 25b although the fluid conduits or tubing 25a, 25b may be directly inserted into the bores 28a, 28b if desired, thereby eliminating the couplings. The fluid conduits or tubing 25a, 25b are inserted in the instrument tube 12 alongside push rod 14. The proximal end of each flexible fluid conduit is preferably coupled to a second fluid coupling 23a, 23b located on the proximal actuating means 16 as shown in FIG. 1. This fluid coupling may be provided with separate lumens 23a, 23b for each respective fluid conduit 25a, 25b whereby the flow of fluid through the separate end effectors 18a, 18b may be separately controlled. Those skilled in the art will appreciate that with this configuration, one end effector, e.g. 18a, may be supplied with a source of irrigation fluid 32 through conduit 25a via lumen 23a, while the other end effector, 18b, may be supplied with a source of suction 34 through conduit 25b via lumen 23b in fluid coupling 23. Alternatively, both end effectors may be supplied with either suction or irrigation and the conduits 25a, 25b may be joined in a single lumen in fluid coupling 23a/23b. Further, if both end effectors 18a, 18b are to be supplied only with suction or only with irrigation, it will be appreciated that separate conduits 25a, 25b are not needed. In such a configuration, a single conduit may be provided with a Y-adapter (not shown) at the distal end to couple to both fluid couplings 27a, 27b of end effectors 18a, 18b. It will also be appreciated that, if desired, only one of the end effectors need be provided with a fluid bore, and only one conduit need be provided.

Figure 2:
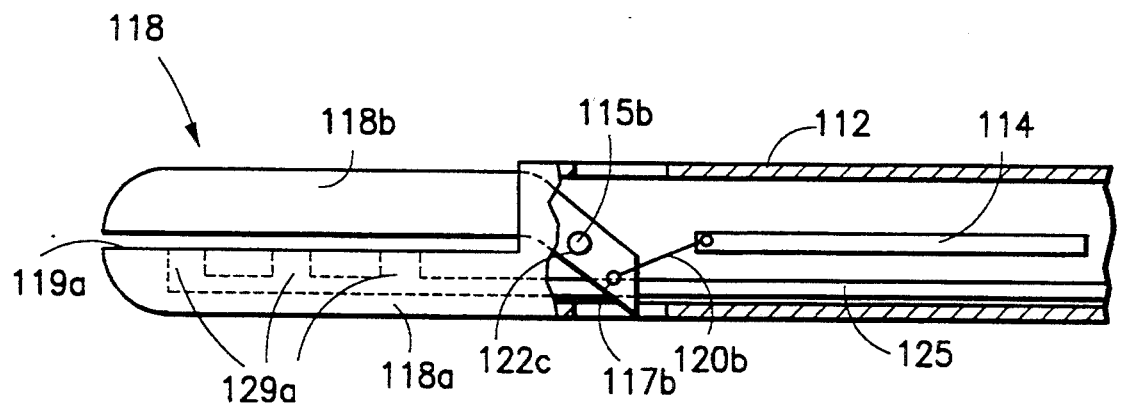
FIG. 2 is an enlarged broken side elevation view in partial section of a second embodiment of the invention.
Figure 2A:
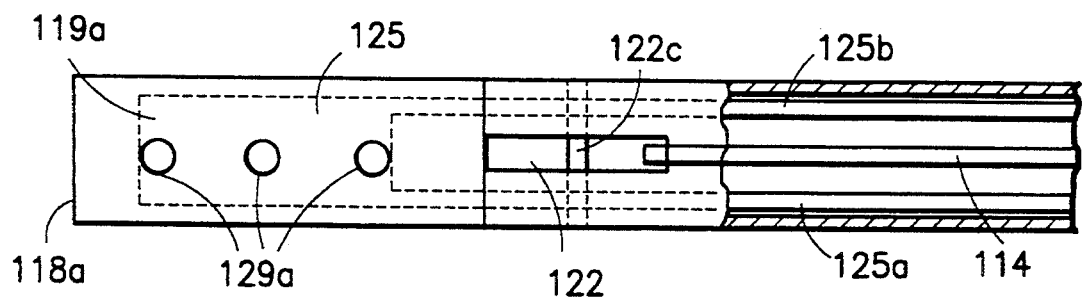
FIG. 2a is an enlarged broken top view in partial section of the stationary end effector of the embodiment of FIG. 2.
Figure 2B:
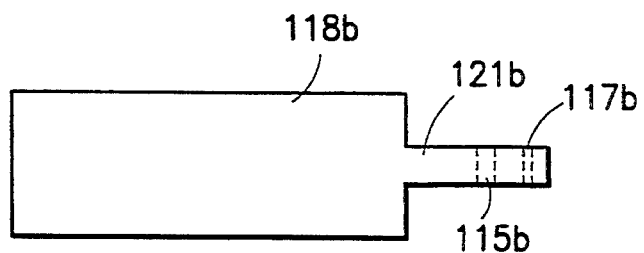
FIG. 2b is an enlarged top view of the movable end effector of the embodiment of FIG. 2.

Turning now to FIGS. 2, 2a, and 2b, in a second embodiment of the invention the distal end of tube 112 comprises an integral fixed end effector 118a and is provided with a central slot-like opening 122 for receiving the central tang 121b of a movable end effector 118b. The movable end effector 118b is provided with a pivot hole 115b and a coupling hole 117b in its tang 121b. The tang 121b is inserted into the slot-like opening 122 and held in rotational engagement therewith by a pivot pin 122c. The coupling hole 117b is coupled to a push rod 114 by an articulable linkage 102b in a manner similar to that described above. In this embodiment, axial movement of the push rod 114 effects a rotational movement of end effector 118b while end effector 118a remains stationary.

In this second embodiment of the invention, the integral stationary end effector 118a is provided with one or more fluid openings 129a on its inner face 119a, although a fluid opening could be provided at the distal end of the stationary end effector 118a if desired. These openings 129a are in fluid communication with an internal fluid conduit 125 which extends through the tube 112 to a proximal fluid coupling (not shown) similar to that shown in FIG. 1, above. As seen in FIG. 2a, fluid conduit 125 may branch into two parallel conduits 125a, 125b to avoid the central slot-like opening 122. Alternatively, fluid conduit 125 may branch to either side 125a, 125b alone. In the configuration shown in FIG. 2a, one branch, e.g. 125a, of the fluid conduit may be coupled to a source of irrigation (not shown) and the other branch 125b coupled to a source of suction (not shown). Further, fluid openings 129a may be separately coupled to different branches 125a, 125b of the fluid conduit so that some openings provide irrigation while others supply suction. Those skilled in the art will appreciate that in this embodiment, the fluid conduit(s) 125 (125a, 125b) need not be flexible and can be formed as lumens in the tube 112.

Figure 3A:
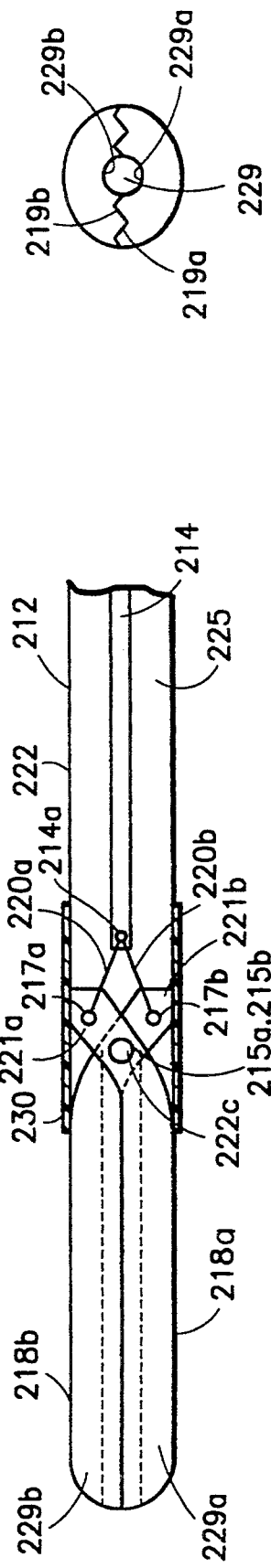
FIG. 3a is a distal end view of the embodiment of FIG. 3.
Figure 3:
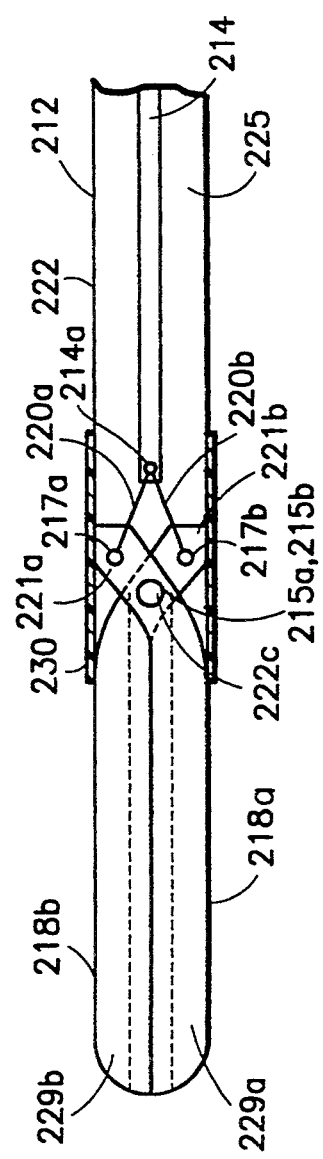
FIG. 3 is an enlarged broken side elevation view in partial section of a third embodiment of the invention.

A third embodiment of the invention is shown in FIGS. 3 and 3a. This embodiment is similar to the first embodiment described above in that a double acting pair of end effectors 218a, 218b are mounted for rotation in a clevis 222 about a clevis pin 222c though pivot holes 215a, 215b. The tangs 221a, 221b of the end effectors 218a, 218b are coupled to the push rod 214 by links 220a, 220b which extend from a distal hole 214a in the push rod 214 to the linkage holes 217a, 217b of the tangs. Axial movement of push rod 214 effects a rotational movement of both end effectors 218a, 218b in substantially the same manner as described above with regard to the first embodiment.

In this third embodiment, the end effectors 218a, 218b are each provided with a central longitudinal groove 229a, 229b on their respective inner face surfaces 219a, 219b. As seen best in FIG. 3a, when the end effectors 218a, 218b are in the closed position, these longitudinal grooves 229a, 229b form a cylindrical throughbore 229 which is open at the distal end of the end effectors and is in fluid communication with the annular interior 225 of tube 212 surrounding push rod 214. An elastic sleeve 230 is provided around the clevis 222 in the vicinity of the clevis pin 222c. The elastic sleeve 230 effectively seals fluid communication between the throughbore 229 and an annulus 225 formed between the tube 212 and the push rod 214, while still allowing rotational movement of the end effectors 218a, 218b. The proximal end (not shown) of tube 212 is coupled to a source of irrigation fluid (not shown) and/or a source of suction (not shown) in a manner similar to that described above with reference to FIG. 1. In this embodiment, therefore, suction and/or irrigation may be supplied to the end effectors through the annulus 225 of tube 212 when the end effectors 218a, 218b are in the closed position as shown in FIGS. 3 and 3a. Moreover, depending on the dimensions of the grooves 229a, 229b, suction and/or irrigation can also be made available between the end effectors when they are in the opened position.

As seen in FIG. 3a, the inner face surfaces 219a, 219b of end effectors 218a, 218b are preferably provided with mating longitudinal ribs which help guarantee a fluid tightness when the end effectors are closed. Those skilled in the art will appreciate that by expanding on the embodiment disclosed in FIGS. 3 and 3a, the end effectors can be formed as a cutting/ripping tool rather than as a gripping or dissecting tool. That is, by sharpening the ribs and increasing their inclination, mating cutting edges may be formed on the inner surfaces of the end effectors.

There have been described and illustrated herein several embodiments of an endoscopic instrument with end effectors incorporating or forming a suction and/or irrigation lumen. While particular embodiments of the invention have been described, it is not intended that the invention be limited thereto, as it is intended that the invention be as broad in scope as the art will allow and that the specification be read likewise. Thus, while particular configurations of fluid openings on the faces of end effectors have been disclosed, it will be appreciated that other locations and configurations of one or more fluid openings could be utilized. Also, while particular shapes and locations of fluid conduits have been shown, it will be recognized that other types of fluid conduits could be used to couple a fluid source with the fluid openings in the end effectors with similar results obtained. Moreover, while particular configurations have been disclosed in reference to the shapes and surfaces of the end effectors, it will be appreciated that other configurations could be used as well and that the disclosed invention could be applied to many different types of end effectors. It will also be appreciated that different aspects of the different embodiments of the invention can be combined to form yet other embodiments of the invention. Furthermore, while the fluid conduit discussed herein has been disclosed as being for suction and/or irrigation, it will be understood that the suction and/or irrigation lumen of the invention can be used with other fluids such as medicaments, etc. It will therefore be appreciated by those skilled in the art that yet other modifications could be made to the provided invention without deviating from its spirit and scope as so claimed.

I claim:

1. An endoscopic surgical instrument comprising:
   a) a hollow tube having a proximal end and a distal end;
   b) a pair of end effector elements, at least one of said end effector elements pivotally coupled to said hollow tube, and at least one of said pair of end effector elements defining or being provided with a first fluid passageway which has a proximal fluid opening and which terminates in at least one distal fluid opening located distally of said starting location;
   c) actuating means extending at least partially through said hollow tube for coupling to at least one of said pair of end effector elements and for causing at least one of said pair of end effector elements to pivot upon actuation of said actuating means; and
   d) fluid conduit means having a proximal end and a distal end for conducting fluid through said hollow tube, said distal end of said fluid conduit means being coupled to said first fluid passageway; wherein
   said first fluid passageway comprises a longitudinal groove on a surface of a first of said pair of end effector elements, said groove extending to a distal tip of said surface, and said at least one distal fluid opening is located at said distal tip of said surface such that said distal fluid opening is not obstructed when said end effector elements are in a closed position.

2. An endoscopic instrument according to claim 1, wherein:
a first of said pair of end effector elements is provided with said first fluid passageway, and a second of said pair of end effector elements is provided with a second fluid passageway having a second proximal fluid opening and a second distal fluid opening.

3. An endoscopic instrument according to claim 2, wherein:
said fluid conduit means comprises a first fluid conduit and a second fluid conduit, said first fluid conduit being coupled to said first fluid passagway, and said second fluid conduit being coupled to said second fluid passageway.

4. An endoscopic instrument according to claim 3, further comprising:
fluid coupling means located at a proximal end of said endoscopic instrument.

5. An endoscopic instrument according to claim 4, for use in conjunction with a source of suction and a source of irrigation fluid, wherein:
said fluid coupling means comprises a first fluid coupler and a second fluid coupler, said first fluid coupler being coupled to said first fluid conduit and said second fluid coupling means being coupled to said second fluid conduit, wherein
said first fluid coupler is coupled to the source of suction and said second fluid coupler is coupled to the source of irrigation fluid.

6. An endoscopic instrument according to claim 1, wherein:
said fluid conduit means is integral with said tube.

7. An endoscopic instrument according to claim 1, wherein:
said at least one fluid opening comprises a plurality of fluid openings on a surface of said at least one of said end effector elements having a fluid passage.

8. An endoscopic instrument according to claim 1, wherein:
one of said end effector elements is stationary relative to said tube, and said first fluid passageway and said at least one distal fluid opening are located in said end effector element which is stationary.

9. An endoscopic instrument according to claim 8, wherein:
said at least one distal fluid opening comprises a plurality of distal fluid openings on a surface of said end effector element which is stationary.

10. An endoscopic instrument according to claim 1, wherein:
said first fluid passageway comprises a second longitudinal groove on a second surface of said second of said pair of end effector elements, said first surface and said second surface facing each other.

11. An endoscopic instrument according to claim 10, wherein:
said first surface of said first of said pair of end effector elements is provided with at least a first longitudinal rib, and said second surface of said second of said pair of end effector elements is provided with at least a second longitudinal rib, said first longitudinal rib and said second longitudinal rib mating with each other.

12. An endoscopic instrument according to claim 10, wherein:
said fluid conduit means comprises an annular space between said hollow tube and said actuating means extending through said hollow tube.

13. An endoscopic instrument according to claim 12, further comprising:
an elastic fluid seal coupling said distal end of said tube and said pair of end effector elements.

14. An endoscopic instrument according to claim 1, further comprising:
a clevis means located at said distal end of said hollow tube and acting to couple said hollow tube and said pair of end effector elements, wherein
said actuation means comprises a rod and a handle coupled to a proximal end of said rod.

15. An endoscopic instrument according to claim 14, further comprising:
connecting means for linking a distal end of said rod with said at least one end effector pivotally coupled to said tube.

16. An endoscopic instrument according to claim 1, for use in conjunction with at least one of a source of suction and a source of irrigation fluid, further comprising:
fluid coupling means coupled to said proximal end of said fluid conduit means, said fluid coupling means being in fluid communication with at least one of the source of suction and the source of irrigation fluid.

17. An endoscopic surgical instrument comprising:
a) a hollow tube having a proximal end and a distal end;
b) a pair of end effector elements, at least one of said end effector elements pivotally coupled to said hollow tube, and at least one of said pair of end effector elements defining or being provided with a first fluid passageway which has a proximal fluid opening and which terminates in at least one distal fluid opening located distally of said starting location;
c) actuating means extending at least partially through said hollow tube for coupling to at least one of said pair of end effector elements and for causing at least one of said pair of end effector elements to pivot upon actuation of said actuating means; and
d) fluid conduit means having a proximal end and a distal end for conducting fluid through said hollow tube, said distal end of said fluid conduit means being coupled to said first fluid passageway, wherein
said fluid conduit means comprises an annular space between said hollow tube and said actuating means.

18. An endoscopic instrument according to claim 17, further comprising:
e) an elastic fluid seal coupling said distal end of said tube and said pair of end effector elements.

* * * * *